United States Patent

Ikeda et al.

[11] Patent Number: 5,906,921
[45] Date of Patent: May 25, 1999

[54] BIOSENSOR AND METHOD FOR QUANTITATIVE MEASUREMENT OF A SUBSTRATE USING THE SAME

[75] Inventors: Shin Ikeda, Katano; Toshihiko Yoshioka; Shiro Nankai, both of Hirakata, all of Japan

[73] Assignee: Matsushita Electric Industrial Co., Ltd., Osaka, Japan

[21] Appl. No.: 09/159,686

[22] Filed: Sep. 24, 1998

[30] Foreign Application Priority Data

Sep. 29, 1997 [JP] Japan .................................. 9-263483
Sep. 29, 1997 [JP] Japan .................................. 9-263492

[51] Int. Cl.$^6$ ................................ C12Q 1/26; C12Q 1/54; C12Q 1/00
[52] U.S. Cl. .................................. 435/25; 435/14; 435/4; 435/82.01; 435/289.1; 435/817; 435/283.1; 435/285.2; 435/287.1; 422/50; 422/68.1; 422/82.01; 422/82.02; 422/82.03
[58] Field of Search ................................ 435/25, 14, 4, 435/82.01, 289.01, 817, 283.1, 285.2, 287.1; 422/50, 68.1, 82.01, 82.02, 82.03

[56] References Cited

U.S. PATENT DOCUMENTS 5,120,420 6/1992 Nankai et al. ............................ 435/25
5,264,103 11/1993 Yoshioka et al. ......................... 435/25
5,582,697 12/1996 Ikeda et al. ............................... 435/25
5,650,062 7/1997 Ikeda et al. ............................... 435/25
5,651,869 7/1997 Yoshioka et al. ......................... 435/25

FOREIGN PATENT DOCUMENTS 03202764 4/1991 Japan .

*Primary Examiner*—Louise N. Leary
*Attorney, Agent, or Firm*—McDermott, Will & Emery

[57] ABSTRACT

A biosensor is disclosed for application to a method for quantitative measurement of a substrate comprising a first step of causing a substrate contained in a sample to react with an oxidoreductase specific to the substrate in the presence of an electron mediator in oxidized state, a second step of applying a potential to a working electrode for reducing the electron mediator in oxidized state that remains not reduced in the first step, and a third step of measuring a reduction current flowing across the working electrode and a counter electrode. The biosensor comprises an electrically insulating base plate, an electrode system having a working electrode and a counter electrode formed on the base plate, and a reaction layer which is formed on or in the vicinity of the electrode system and contains at least an oxidoreductase and an electron mediator, the counter electrode including at least a reductant of a redox compound or an electrolytically oxidizable metal.

6 Claims, 2 Drawing Sheets

BIOSENSOR AND METHOD FOR QUANTITATIVE MEASUREMENT OF A SUBSTRATE USING THE SAME

BACKGROUND OF THE INVENTION

The present invention relates to a biosensor for facilitating simple and high accuracy quantitation of a substrate and a method for quantitative measurement of a substrate using the same.

There has been a conventional simple method for quantitating a specific component in a sample solution with no dilution or agitation of the sample solution. This method causes the specific component to react with an oxidoreductase whose substrate corresponds to the specific component in the presence of an electron mediator or electron acceptor and subsequently oxidizes the electron mediator reduced by the enzyme reaction electrochemically. The concentration of the specific component is then determined from the oxidation current flowing during this electrochemical oxidation.

This method normally uses a biosensor as disclosed in Japanese Laid-Open Patent Publication No. 2,517,153.

The biosensor is produced by first forming an electrode system having a working electrode and a counter electrode on an electrically insulating base plate by a screen printing method or the like, subsequently forming a reaction layer including an oxidoreductase and an electron mediator on the electrode system, and finally bonding a cover and a spacer to the electrically insulating base plate.

This biosensor facilitates quantitation of various specific components by varying the oxidoreductase.

A glucose sensor will be described as an example of biosensor.

Conventionally known method for quantitative measurement of glucose is a system comprising a combination of glucose oxidase with an oxygen electrode or a hydrogen peroxide electrode (e.g., "Biosensor", ed. by Shuichi Suzuki, Kodansha, Japan).

Glucose oxidase selectively oxidizes a substrate β-D-glucose to D-glucono-δ-lactone by utilizing oxygen dissolved in a sample solution as an electron mediator. When the substrate is oxidized by the glucose oxidase, the oxygen used as the electron mediator is reduced to hydrogen peroxide. The glucose concentration can be quantitated either by measurement of the volume of oxygen consumed during this reaction using an oxygen electrode or by measurement of the volume of hydrogen peroxide produced using a hydrogen peroxide electrode of platinum or the like.

However, this method has a drawback that the measurement is largely affected by the concentration of oxygen contained in a sample solution, depending on the measuring object. This system has another drawback that the system cannot function in the absence of oxygen.

To overcome these problems, a type of glucose sensor has been developed which includes an organic compound or a metal complex such as potassium ferricyanide, ferrocene derivatives, quinone derivatives, etc. as electron mediator, in place of oxygen.

This biosensor can carry a known amount of glucose oxidase on an electrode system, together with an electron mediator in their stabilized state. This structure enables to combine the electrode system with the reaction layer integrally almost in dry state.

Such biosensor is normally disposable and facilitates measurement of the concentration of glucose by a simple instillation of a measuring sample at a sensor chip mounted in a measurement device. Therefore, this biosensor has been attracting much attention recently.

As described above, the substrate in a sample can be quantitated based on the current required for oxidizing the reductant of the electron mediator which has been produced by a series of enzyme reaction on the electrode.

However, some samples are assumed to contain an easy-to-oxidize substance which is oxidized upon oxidation of an electron mediator in reduced state on the electrode to generate an oxidation current and hence produces a positive error in the current value measured. Moreover, if the measuring sample contains a high concentration of substrate, the oxidation current value may vary.

In order to solve these problems, the present inventors propose a method for quantitative measurement of a substrate based on the reduction current value which flows during reduction of the electron mediator in oxidized state on the working electrode which remains not reduced by a series of enzyme reaction. This method precludes adverse effects of any easy-to-oxidize substance on the measurement results.

However, if the reduction current value is measured with a two-electrode system comprising a working electrode and a counter electrode, then the presence of some amount of electron mediator in reduced state which must be oxidized on the counter electrode in correspondence with the reduction of already oxidized electron mediator on the working electrode becomes mandatory. With this system, however, if the substrate concentration is predicted to be low, the electron mediator in reduced state may be depleted, which renders the oxidation on the counter electrode to develop a rate-determining step that adversely affects the reduction current value measured.

BRIEF SUMMARY OF THE INVENTION

The object of the present invention is therefore to provide a biosensor facilitating high accuracy quantitation of a substrate concentration in a sample by eliminating the above-mentioned inconveniences.

Another object of the present invention is to provide a method for simple and high performance quantitative measurement of a substrate with high accuracy with the aid of this biosensor.

The present invention provides a biosensor comprising an electrically insulating base plate, an electrode system having a working electrode and a counter electrode formed on the base plate, and a reaction layer which is formed on or in the vicinity of the electrode system and contains at least an oxidoreductase and an electron mediator, wherein the counter electrode includes at least a reductant of a redox compound or a metal permitting electrolytic oxidation.

The present invention also provides a method for quantitative measurement of a substrate by using the above-mentioned biosensor, comprising a first step of adding a sample to the reaction layer to cause a substrate contained in the sample to react with an enzyme contained in the reaction layer, a second step of applying a potential to the working electrode for reducing the electron mediator in oxidized state that remains not reduced in the course of the first step, and a third step of measuring a reduction current flowing across the working electrode and the counter electrode.

In a preferred mode of the invention, the counter electrode includes ferrocene or a ferrocene derivative as the redox compound.

In another preferred mode of the invention, the counter electrode includes silver or copper as the electrolytically oxidizable metal.

In still another preferred mode of the invention, the counter electrode is composed of a mixture of at least an electrolytically oxidizable metal with carbon.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
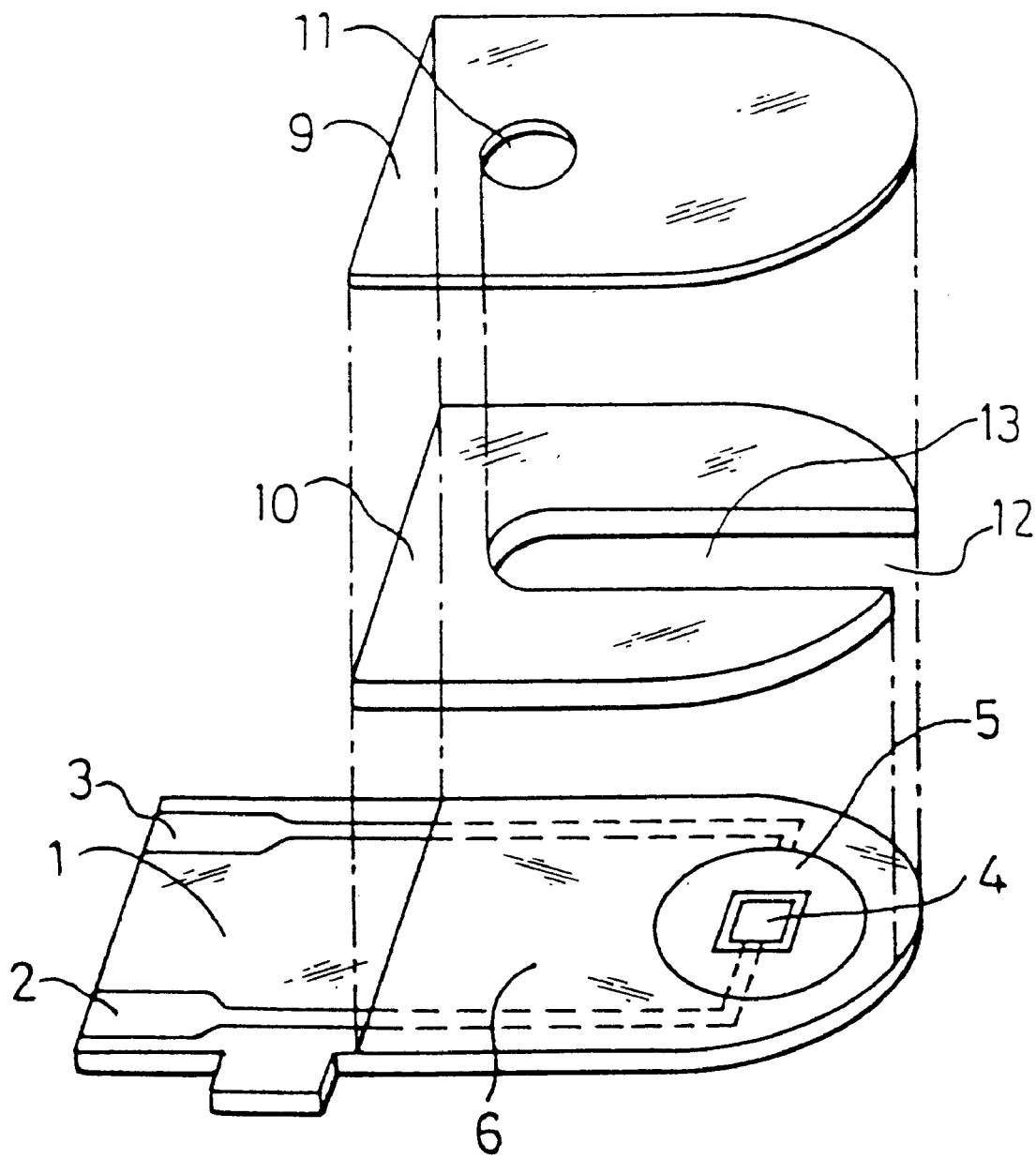
FIG. 1 is an exploded perspective view of a glucose sensor with an omission of the reaction layer in one example of the present invention.

As stated above, the method for quantitative measurement of a substrate in accordance with the present invention adds a sample to the reaction layer to cause the substrate to react with the enzyme. As the enzyme reaction proceeds, the electron mediator contained in the reaction layer is reduced to the extent to reflect the concentration of substrate in the sample. Then, a potential is applied to the working electrode to reduce the electron mediator in oxidized state which remains not reduced during the enzyme reaction thereby to generate reduction current. The substrate concentration is then determined by measuring the reduction current flowing across the two electrodes.

In this method, if the amount of electron mediator is held at a constant level in the reaction layer, the reduction current reflects the concentration of substrate in the sample sharply. Therefore, if a reduction current value of a standard solution containing a known amount of substrate is calibrated preliminarily to obtain a reference calibration curve, the substrate concentration in a sample can be quantitatively determined based on the reference.

As such, the present invention quantifies a substrate based on the reduction current, which prevents the reduction current from being adversely affected by, if any, the presence of an easy-to-oxidize substance.

Furthermore, as described above, the counter electrode includes at least a reductant of a redox compound or an electrolytically oxidizable metal. This configuration prevents the oxidation on the counter electrode from entering the rate-determining step in the course of measurement of reduction current values on the working electrode, even if the sample contains a low concentration of substrate and hence the available electron mediator in reduced state generating by the enzyme reaction is small in amount.

The biosensor in accordance with the present invention includes an improved counter electrode, which precludes a concern about influences of the counter electrode on sensor preservation. Certain redox compounds may have adverse effects on the sensor preservation; therefore, if a redox compound is to be added to the enzyme layer, it is essential to examine its effect preliminarily. The present invention includes a reductant of a redox compound or an electrolytically oxidizable metal in the counter electrode, which configuration produces an advantage that they can be added in a larger amount if the substrate concentration is high, compared to a biosensor which adds those components in the reaction layer.

It is better that the amount of redox compound or electrolytically oxidizable metal to be contained in the counter electrode is larger than the amount of electron mediator to be contained in the reaction layer.

Preferably used redox compounds may be exemplified as ferrocene, a ferrocene derivative such as vinyl ferrocene, a metal complex, hydroquinone, etc.

On the other hand, preferred electrolytically oxidizable metal includes silver and copper, but iron, zinc and the like may also be used.

This metal can be ground into a powder and mixed with a binder to make a paste for use in the counter electrode by printing the paste directly on a base plate. This simplifies the manufacturing process of a sensor.

A counter electrode comprising a mixture of a powder of the metal with a carbon powder and a binder can reduce the production cost, which is preferable.

It is also preferable to coat the entire surface of the electrode system formed on the base plate with a layer of a hydrophilic polymer so as to avoid possible contact of the enzyme and electron mediator in the reaction layer or possible adsorption of protein in the sample with or onto the surface of the electrode system.

Available hydrophilic polymers for forming the hydrophilic polymer layer include polyvinyl pyrrolidone, polyvinyl alcohol, polyamino acid such as polylysine, polystyrene sulfonate, gelatin and its derivative, a polymer of acrylic acid or an acrylate, a polymer of methacrylic acid or a methacrylate, starch and its derivative, a polymer of maleic anhydride or a maleate, cellulose derivatives such as carboxymethyl cellulose, hydroxypropyl cellulose, methyl cellulose, ethyl cellulose, hydroxyethyl cellulose, ethylhydroxyethyl cellulose, carboxymethylethyl cellulose or the like. Among them, carboxymethyl cellulose, hydroxyethyl cellulose, hydroxypropyl cellulose, methyl cellulose, ethyl cellulose, ethylhydroxyethyl cellulose and carboxymethylethyl cellulose are preferred.

As the electron mediator to be contained in the reaction layer, potassium ferricyanide, p-benzoquinone, phenazine methosulfate, methylene blue, ferrocene derivatives, or the like may be used.

Applicable oxidoreductases include glucose oxidase, glucose dehydrogenase, alcohol oxidase, lactate oxidase, lactate dehydrogenase, fructose dehydrogenase, uricase, cholesterol oxidase, cholesterol esterase, xanthine oxidase, amino acid oxidase and the like.

A combination of plural oxidoreductases may also be used, for example, glucose oxidase plus invertase, glucose oxidase plus invertase plus mutarotase, fructose dehydrogenase plus invertase, or the like.

The enzyme and the electron mediator may be dissolved in the sample solution, or prevented from being dissolved in the sample solution by fixing the reaction layer to the base plate. If the latter configuration is adopted, it is preferred for the reaction layer to further contain one of the hydrophilic polymers exemplified above.

The reaction layer may further contain a pH buffer. The pH buffer may be exemplified as potassium dihydrogen phosphate-dipotassium phosphate, potassium dihydrogen phosphate-disodium phosphate, sodium dihydrogen phosphate-dipotassium phosphate, sodium dihydrogen phosphate-disodium phosphate, citric acid-disodium phosphate, citric acid-dipotassium phosphate, citric acidtrisodium citrate, citric acid-tripotassium citrate, potassium dihydrogen citrate-sodium hydroxide, sodium dihydrogen citrate-sodium hydroxide, sodium hydrogen maleate-sodium hydroxide, potassium hydrogen phthalatesodium hydroxide, succinic acid-sodium tetraborate, maleic acid-tris (hydroxymethyl)aminomethane, tris(hydroxymethyl) aminomethane tris(hydroxymethyl)aminoethane hydrochloride, [N-(2-hydroxyethyl)piperazine-N'-2-ethanesulfonic acid]-sodium hydroxide, [N-tris (hydroxymethyl)methyl-2-aminoethanesulfonic acid]-sodium hydroxide, and [piperazine-N,N'-bis(2-ethanesulfonic acid)]-sodium hydroxide.

A lecithin layer may also be formed on the reaction layer for smooth supply of a sample solution.

In the following, the present invention will be described specifically by way of concrete examples.

In the below-mentioned examples, although the working electrode, the counter electrode and the insulating layer were formed by specific printing patterns, the present invention is not limited to those patterns. Similarly, the voltage to be applied to the electrode is not limited to that used in the below-mentioned examples.

FIG. 1 shows an exploded perspective view of a two-electrode system glucose sensor with an omission of the reaction layer. In the glucose sensor, a silver paste is printed on an electrically insulating base plate 1 of polyethylene terephthalate by the screen printing method so as to form leads 2 and 3 on the base plate 1. Subsequently, a conductive carbon paste containing a resin binder is printed on the base plate 1 so as to form a working electrode 4. The working electrode 4 is in contact with the lead 2. Then, an electrically insulating layer 6 is further formed on the base plate 1 by printing thereon an insulating paste. The electrically insulating layer 6 covers the periphery of the working electrode 4 so as to hold the exposed area of the working electrode 4 constant. Thereafter, a conductive carbon paste containing a resin binder and a redox compound or an electrolytically oxidizable metal, or a silver or copper paste including a resin binder is printed on the base plate 1 so as to cause the paste to contact the previously formed lead 3, which formed a ring-like counter electrode 5.

Then, the electrically insulating base plate 1, a cover 9 having an air vent 11 and a spacer 10 are bonded to each other in a positional relationship as shown by the dotted chain line in FIG. 1, which gives a biosensor used as a glucose sensor in the below-mentioned examples. The spacer 10 has a slit 13 for forming a sample supply path between the base plate and the cover. Numeral 12 corresponds to an opening of the sample supply path.

Figure 2:
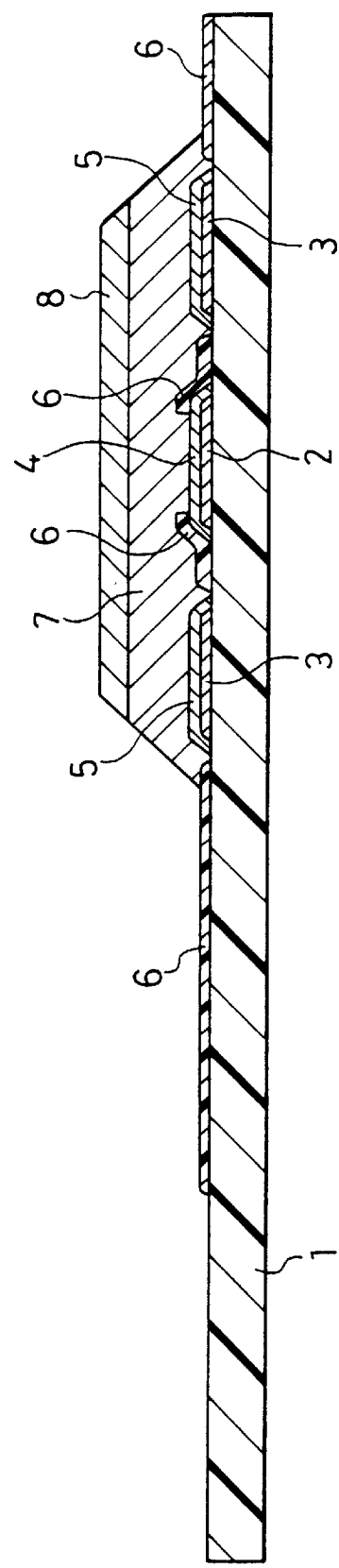
FIG. 2 is a vertical cross-sectional view illustrating the vital part of the glucose sensor with an omission of the spacer and the cover.

FIG. 2 is a vertical cross-sectional view illustrating vital parts of the biosensor in accordance with the present invention from which the spacer and the cover are omitted. On the electrically insulating base plate 1 on which the electrode system is already formed as shown in FIG. 1, a reaction layer 7 containing reagents including an enzyme and an electron mediator is formed, above which a lecithin layer 8 is further formed later.

The reaction layer 7 is preferably formed on the electrode system, but it may be formed in the vicinity of the electrode system, for instance, on the cover side so as to be exposed to the sample supply path.

EXAMPLE 1

As shown in FIG. 1, on the base plate 1, an electrode system having at least a counter electrode of a conductive carbon paste that includes a resin binder and ferrocene as the redox compound was formed first.

Then, the reaction layer 7 was formed by dropping a mixed aqueous solution of glucose oxidase (EC1.1.3.4; hereinafter referred to as "GOD") with potassium ferricyanide on the electrode system and drying it. Subsequently, the lecithin layer 8 was formed by dropping a toluene solution of lecithin on the reaction layer 7 and drying it.

The cover 9 and the spacer 10 were then bonded to the base plate 1 in a positional relationship shown by the dotted chain line in FIG. 1, which gave a glucose sensor used in this example.

As a sample solution, an aqueous glucose standard solution (3 μl) was supplied to the glucose sensor through the opening 12 of the sample supply path. The sample solution advanced to the air vent 11 and dissolved the reaction layer 7 present above the electrode system. Upon dissolution of the reaction layer 7, enzyme reaction where glucose contained in the sample solution is oxidized to gluconolactone by the GOD will take place. This enzyme reaction accompanies at the same time reduction of the ferricyanide ions to ferrocyanide ions.

When a certain time had lapsed after supply of the sample solution, a voltage of −1.0 V was applied to the working electrode 4 with reference to the counter electrode 5, which induced reduction of the potassium ferricyanide which was refractory to the reduction caused by the enzyme reaction on the working electrode. On the counter electrode, on the other hand, oxidation of ferrocene contained in the counter electrode will take place to produce ferricinium ions. The reduction current value flowing across the electrodes was measured 5 seconds after application of the voltage.

The current values measured using various aqueous standard solutions at different glucose concentrations showed decreases with increases in the glucose concentration. This implies that the presence of ferrocene in the counter electrode secured a sufficient amount of a reductant in the reaction system and that the current values depended on the amount of ferricyanide ions to be reduced to ferrocyanide ions on the working electrode. The responsive current value measured with the glucose sensor showed high accuracy.

EXAMPLE 2

In this example, an aqueous solution of carboxymethyl cellulose (hereinafter abbreviated to "CMC") was dropped on the electrode system identical to that of Example 1 and dried to form a CMC layer. The reaction layer and the lecithin layer were formed in this order on the CMC layer in the same manner as in Example 1.

A glucose sensor was produced in the same manner as in Example 1 to measure the sensor responses to various glucose standard solutions. The results showed similar response characteristics for the glucose sensor of this example to those of Example 1, demonstrating less variations.

EXAMPLE 3

In this example, the responsive current value of the glucose sensor was measured in the same manner as in Example 2, except for the use of various aqueous glucose standard solutions containing known amounts of ascorbic acid as the sample solutions.

The results showed that the glucose sensor had similar response characteristics to those of Example 2 which used mere aqueous glucose standard solutions with no ascorbic acid.

Comparative Example 1

As a comparative example, identical glucose sensor and aqueous glucose standard solutions containing ascorbic acid to those of Example 3 were used to measure oxidation current values flowing 5 seconds after application of a voltage of 0.5 V to the working electrode using the counter electrode as reference.

The results showed that the responsive current values were elevated as the amount of ascorbic acid contained in the aqueous glucose standard solution increased.

EXAMPLE 4

A glucose sensor was produced in the same manner as in Example 2 except for the use of vinyl ferrocene as the redox compound and measured for its responses to the aqueous glucose standard solutions. The glucose sensor of Example 4 demonstrated similar response characteristics to those of Example 2.

EXAMPLE 5

A glucose sensor was produced in the same manner as in Example 1 except for the use of a silver paste to form the counter electrode 5 shown in FIG. 1.

Similar to Example 1, an aqueous glucose standard solution (3 μl) as a sample solution was supplied to the glucose sensor through the opening 12 of the sample supply path. The sample solution advanced to the air vent 11 and dissolved the reaction layer 7 present above the electrode system. Upon dissolution of the reaction layer 7, enzyme reaction where glucose contained in the sample solution is oxidized to gluconolactone by the GOD will take place. This enzyme reaction accompanies at the same time reduction of the ferricyanide ions to ferrocyanide ions.

When a certain time had lapsed after supply of the sample solution, a voltage of −0.8 V was applied to the working electrode 4 with reference to the counter electrode 5, which induced reduction of the ferricyanide ions which remained not reduced by the enzyme reaction on the working electrode to generate ferrocyanide ions. On the counter electrode, on the other hand, oxidation of silver contained in the counter electrode will take place to produce silver ions. The reduction current value flowing across the electrodes was measured 5 seconds after application of the voltage. The current values measured using various aqueous glucose standard solutions showed decreases with increases in the glucose concentration. This implies that the presence of silver in the counter electrode secured a sufficient amount of a reductant in the reaction system and that the current values depended on the amount of ferricyanide ions to be reduced to ferrocyanide ions on the working electrode. The responsive current value measured with the glucose sensor showed high accuracy.

EXAMPLE 6

A glucose sensor was produced in the same manner as in Example 5 except for the use of a copper paste in place of silver paste to form the counter electrode 5 and measured for its responses to various aqueous glucose standard solutions. The glucose sensor of this example showed similar response characteristics to those of Example 5.

EXAMPLE 7

Another glucose sensor was produced in the same manner as in Example 5 except for the use of a mixed paste of silver and carbon to form the counter electrode and measured for its responses to various aqueous glucose standard solutions. The glucose sensor of Example 7 showed similar response characteristics to those of Example 5.

EXAMPLE 8

In this example, the responsive current value of the glucose sensor of Example 5 was measured in the same manner as in Example 5, except for the use of various aqueous glucose standard solutions containing known amounts of ascorbic acid as the sample solutions.

The results showed identical response characteristics for the glucose sensor of Example 8 to those of Example 5 which used mere aqueous glucose standard solutions with no ascorbic acid.

Comparative Example 2

As a comparative example, the same glucose sensor as in Example 5 and various aqueous glucose standard solutions containing ascorbic acid as in Example 8 were used. The glucose sensor was applied with a voltage of 0.5 V to the working electrode using the counter electrode as reference and the oxidation current value flowing across the electrodes was measured after 5 seconds. The results showed increased responsive current values with the increases in the ascorbic acid concentration in the aqueous glucose standard solution.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

We claim:

1. A biosensor comprising an electrically insulating base plate, an electrode system having a working electrode and a counter electrode formed on said base plate, and a reaction layer which is formed on or in the vicinity of said electrode system and contains at least an oxidoreductase and an electron mediator, said counter electrode including at least a reductant of a redox compound or a metal permitting electrolytic oxidation.

2. The biosensor in accordance with claim 1, wherein said redox compound is ferrocene or a ferrocene derivative.

3. The biosensor in accordance with claim 1, wherein said counter electrode is composed of a mixture of at least one electrolytically oxidizable metal with carbon.

4. The biosensor in accordance with claim 1, wherein said electrolytically oxidizable metal is silver or copper.

5. The biosensor in accordance with claim 1, wherein said reaction layer further contains a hydrophilic polymer.

6. A method for quantitative measurement of a substrate by using a biosensor which comprises an electrically insulating base plate, an electrode system having a working electrode and a counter electrode including at least a reductant of a redox compound and an electrically oxidizable metal, both being formed on said base plate, and a reaction layer which is formed on or in the vicinity of said electrode system and contains at least an oxidoreductase and an electron mediator, said method comprising:

a first step of adding a sample to said reaction layer to cause a substrate contained in said sample to react with an enzyme contained in said reaction layer, a second step of applying a potential to said working electrode for reducing said electron mediator in oxidized state that remains not reduced in the course of said first step, and a third step of measuring a reduction current flowing across said working electrode and said counter electrode.

* * * * *